(12) United States Patent
Solouki et al.

(10) Patent No.: US 6,745,132 B1
(45) Date of Patent: Jun. 1, 2004

(54) METHOD FOR DETERMINING THE MOLECULAR WEIGHT OF A SUBSTANCE CONTAINED IN A SOLUTION

(75) Inventors: Touradj Solouki, Orono, ME (US); Alireza Fattahi, Minneapolis, MN (US)

(73) Assignee: University of Maine System Board of Trustees, Bangor, ME (US)

( * ) Notice: Subject to any disclaimer, the term of this patent is extended or adjusted under 35 U.S.C. 154(b) by 0 days.

(21) Appl. No.: 10/219,684

(22) Filed: Aug. 15, 2002

Related U.S. Application Data

(60) Provisional application No. 60/312,856, filed on Aug. 16, 2001.

(51) Int. Cl.[7] .............................................. G01N 31/00
(52) U.S. Cl. ........................................ 702/27; 436/102
(58) Field of Search ............................. 702/19, 22, 23, 702/25, 27, 30; 436/68, 102, 539–541; 502/401; 508/390–392

(56) References Cited

U.S. PATENT DOCUMENTS

| | | | | |
|---|---|---|---|---|
| 4,164,474 A | * | 8/1979 | Gallacher et al. ............ 508/390 |
| 4,276,323 A | * | 6/1981 | Oka et al. ...................... 427/8 |
| 4,454,229 A | * | 6/1984 | Zander et al. ................. 436/68 |
| 4,459,149 A | * | 7/1984 | Moran et al. .................. 71/24 |
| 4,554,255 A | * | 11/1985 | Ishii et al. .................... 436/102 |
| 4,620,049 A | | 10/1986 | Schmidt et al. .............. 585/501 |
| 5,001,070 A | * | 3/1991 | Ivaska et al. ................ 205/782 |
| 5,065,336 A | | 11/1991 | Buchelli ....................... 702/30 |
| 5,906,960 A | * | 5/1999 | Sanjay et al. ................ 502/401 |

OTHER PUBLICATIONS

The Standrad Deviants The Supper–Charged World of Chemistry (Part 1), 1996 Cerebellum Corporation.*
Strong–Acid, Carboxly–Group Structures in Fulvic Acid from the Suwannee River, Georgia 2. Major Structures, J.A. Leenheer et al., Environmental Science Technology, vol. 29 (1995), pp. 399–405.

* cited by examiner

Primary Examiner—Marc S. Hoff
Assistant Examiner—Mohamed Charioui
(74) Attorney, Agent, or Firm—MacMillan, Sobanski & Todd, LLC

(57) ABSTRACT

A systematic treatment of chemical equilibria is used to determine the average molecular weight of the Suwannee River fulvic acids directly from aqueous solutions. Additionally, parameters such as equilibrium constant and reaction stoichiometry can be calculated. The measurement of the initial mass of unknown analytes is not needed for the determination.

17 Claims, 2 Drawing Sheets

METHOD FOR DETERMINING THE MOLECULAR WEIGHT OF A SUBSTANCE CONTAINED IN A SOLUTION

CROSS REFERENCE TO RELATED APPLICATIONS

This application and claims the benefit of U.S. Provisional Application No. 60/312,856, filed Aug. 16, 2001.

BACKGROUND OF THE INVENTION

This invention relates in general to measurement of molecular weights and in particular to a method for determining the molecular weight of a substance contained in a solution.

A primary goal of the invention was to determine the average molecular weight of fulvic acids directly from aqueous solutions. Fulvic acids are found in soil and water, and they are traditionally defined according to their solubilities in water. Conventional separation and fractionation techniques can not be used to isolate individual molecular components of fulvic acids. Hence, the study of humic substances is limited to investigating bulk properties of this diverse group.

In the past, a known variety of techniques such as Gel Filtration ChromatograpHy (GFC), Vapor Pressure Osmometry (VPO), Laser-Desorption Fourier Transform ion Cyclotron Resonance Mass Spectrometry (LD FT-ICR MS), and Electrospray Ionization Fourier Transform Ion Cyclotron Resonance Mass Spectrometry (ESI FT-ICR MS) have been used to characterize fulvic acid samples. However, each technique has its own limitations. For example, in GFC method, the absolute molecular weight distributions can not be determined due to calibration difficulties. Vapor Pressure Osmometry is a colligative property; hence, the average molecular weight is affected by the extent of dissociation of fulvic acids. In LD FT-ICR MS and ESI FT-ICR MS, during the ionization and detection events, collisions and other energetic processes generally induce fragmentation and/or adduct formation.

It is also known to use pyrolysis/methylation to identify the constituents of fulvic acid samples. For example, pyrolysis reveals the presence of carboxyl groups in alipHatic and aromatic structures. Nevertheless, due to ion fragmentation and side reactions that occur during the pyrolysis process, this technique can not be used to obtain the average molecular weight of fulvic acids.

Accordingly, it would be desirable to provide a simple process for determination of the average molecular weight of fulvic acids.

SUMMARY OF THE INVENTION

This invention relates to a method for determining the molecular weight of a substance contained in a solution.

The invention involves a new approach to calculate the average molecular weight of the Suwannee River fulvic acids in solution phase. Successive disturbances of a reaction at equilibrium and unique mass balance relationships after each disturbance are used to acquire reaction parameters such as stoichiometry, molar concentrations, and molecular weights of the species present in solution/reaction.

More specifically, the invention contemplates a method for determining the molecular weight of a substance that includes providing a first solution containing the substance, the first solution being in chemical equilibrium. A first pH of the first solution is measured. Then a predetermined amount of a standard solution is added to the original solution to form a second solution. After allowing the second solution to reach chemical equilibrium, a second pH of the second solution is measured. A predetermined amount of a standard solution is added to the second solution to form a third solution and, after allowing the third solution to reach chemical equilibrium, a third pH of the third solution is measured. The first, second and third pH's are then used to develop a set of equations that are simultaneously solved to calculate the molecular weight of the substance contained in the first solution.

It is further contemplated that the standard solution that is added can be either an acidic or an alkaline solution.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

Figure 1:
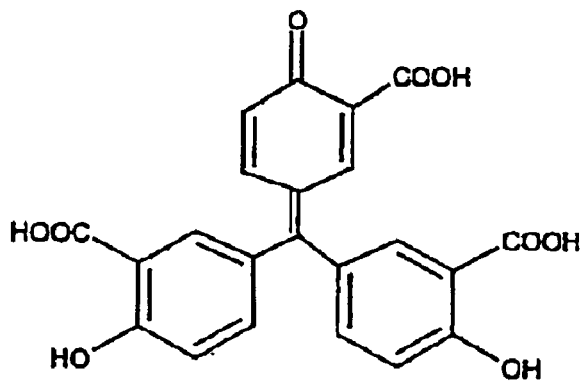
FIG. 1 illustrates the chemical structures of typical compounds that can be analyzed by the present invention.
Figure 1:
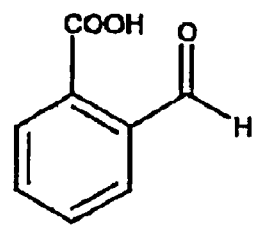
Figure 1:
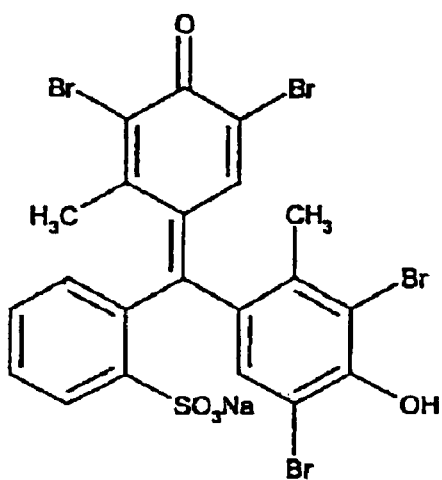

Referring now to the drawings, there is shown in FIG. 1, the molecular structures of typical compounds that can be analyzed by the present invention. For a multiprotic acid such as aurintricarboxylic acid, as shown in FIG. 1A, with p number of is acidic protons, the following acid dissociation reaction can be written:

$$H_pY \rightleftharpoons H^+ + H_{(p-1)}Y^- \tag{a}$$

At the equilibrium, if any acid (i.e., $H^+$) is added to this reaction, according to Le Châtelier's principle, equilibrium concentrations will shift to relieve the effect of this applied stress. For example, after adding $H^+$ to the solution, $H_{(p-1)}Y^-$ will react with $H^+$ to form $H_pY^-$. Moreover, the added $H^+$ common ion will suppress dissociation of $H_{(p-1)}Y^-$ in reaction (a) and relative concentrations of $H_{(p-q)}Y^{q-}$ species, where q>1, will be negligible. Hence, in the following, we only consider the dissociation of the first acidic proton (i.e., $K_{a1}$) and to simplify the notation we consider the reaction (a) as follows:

$$HY \rightleftharpoons H^+ + Y^- \tag{b}$$

At a given temperature T, after disturbing the equilibrium (e.g., by adding a specified amount of a standard acid to the solution), a new equilibrium state will be re-established. According to the mass balance relationships, the initial equilibrium concentrations (i.e., prior to disturbance) can be correlated to the new equilibrium concentrations (i.e., post disturbance). The dissociation constant for the reaction (b) can be written as follows:

$$K_{eq} = \frac{[H^+]_n [Y^-]_n}{[HY]_n} \tag{1}$$

In Eq. (1), n denotes the equilibrium number. For instance, n=1 indicates the initial equilibrium and n=2 represents the equilibrium set up after the first disturbance. In Eq. (1), we can replace the concentration of each component with the corresponding number of moles using the simple relation $m_j$=[j] V, where $m_j$, [j], and V indicate the number of moles, molar concentration, and volume of the solution, respectively. Hence, $K_{eq}$ in terms of $m_j$ and V is:

$$K_{eq} = \frac{m_{H^+_n} m_{Y^-_n}}{m_{HY_n} V_n^3} \qquad (2)$$

In the reaction (b), $[H^+]_n$ can be measured with a pH meter and hence, considering Eq. (1) and the first equilibrium (n=1), there are three unknown parameters: $K_{eq}$, $[Y^-]_1$, and $[HY]_1$. If the volume $V_s$ of a standard acidic solution ($[H^+]_s$) is added to the solution at the initial equilibrium, a connection between the second and first equilibrium states can be established using the mass balance equations. After adding the volume $V_s$ or $m_{H^+}$ moles of acidic standard solution ($m_{H^+}$=$[H^+]_s$, $V_s$), according to the mass balance relationships, $x_1$ moles of $H^+$ and $x_1$ moles of $Y^-$ will be consumed; in contrast, $x_1$ moles will be added to the number of moles of HY. Therefore, the number of moles and concentrations of components present in the reaction vessel at the new (second equilibrium) will be:

$$m_{H^+_2} = m_{H^+_1} + m_{H^+_s} - x_1 \quad (3.1) \quad [H^+]_2 = \frac{m_{H^+_2}}{(V_1 + V_s)} \quad (3.2)$$

$$m_{Y^-_2} = m_{Y^-_1} - x_1 \qquad (4.1) \Rightarrow [Y^-]_2 = \frac{(m_{Y^-_1} - x_1)}{(V_1 + V_s)} \quad (4.2)$$

$$m_{HY_2} = m_{HY_1} + x_1 \qquad (5.1) \Rightarrow [HY]_2 = \frac{(m_{HY_1} + x_1)}{(V_1 + V_s)} \quad (5.2)$$

In Eq. (3.1), $m_{H^+}$ is known ($m_{H^+}$=$[H^+]_s$, $V_s$), $m_{H^+_1}$ and $m_{H^+_2}$ at the first and second equilibrium states can be calculated from the equation $m_{H^+}$=$[H^+]_n V_n$ (where $[H^+]_n$ is determined with a pH meter). Therefore, from Eq. (3.1), $x_1$ can be calculated:

$$x_1 = m_{H^+_1} + m_{H^+_s} - m_{H^+_2} \qquad (6)$$

By substituting the equations (3.2, 4.2, and 5.2) into the equation (1), $K_{eq}$ at the second equilibrium can be written as:

$$K_{eq} = \frac{m_{H^+_2}(m_{Y^-_1} - x_1)}{(m_{HY_1} + x_1)(V_1 + V_s)} \qquad (7)$$

In a same manner, if the second equilibrium is disturbed by adding additional volume $V_s$ of the standard acidic solution $[H+]_s$, the equilibrium concentrations of the third equilibrium can be correlated to those at the first equilibrium. After disturbing the second equilibrium, $x_2$ moles of $H^+$ and $x_2$ moles of $Y^-$ will be consumed; in contrast, $x_2$ moles will be added to the number of moles of HY. Therefore, the number of moles and concentrations of components at the third equilibrium will be:

$$m_{H^+_3} = m_{H^+_2} + m_{H^+_s} - x_2 \qquad (8.1) \quad [H^+]_3 = \frac{m_{H^+_3}}{(V_1 + V_s)} \qquad (8.2)$$

$$m_{Y^-_3} = m_{Y^-_2} - x_2 \xrightarrow{Eq\ (4.1)} m_{Y^-_3} = m_{Y^-_1} - x_1 - x_2 \quad (9.1) \Rightarrow [Y^-]_3 = \frac{(m_{Y^-_1} - x_1 - x_2)}{(V_1 + 2V_s)} \quad (9.2)$$

$$m_{HY_3} = m_{HY_2} + x_2 \xrightarrow{Eq.\ (5.1)} m_{HY_3} = m_{HY_1} + x_1 + x_2 \quad (10.1) \Rightarrow [HY]_3 = \frac{(m_{HY_1} + x_1 + x_2)}{(V_1 + 2V_s)} \quad (10.2)$$

where $x_2$ can be calculated from the mass balance:

$$x_2 = m_{H^+_2} + m_{H^+_s} - m_{H^+_3} \qquad (11)$$

Thus, by substituting the equations (8.2, 9.2, and 10.2) into the equation (1), $K_{eq}$ at the third equilibrium state after the second disturbance can be written as:

$$K_{eq} = \frac{m_{H^+_3}(m_{Y^-_1} - x_1 - x_2)}{(m_{HY_1} + x_1 + x_2)(V_1 + 2V_s)} \qquad (12)$$

Likewise, if we disturb the initial equilibrium n−1 times, $K_{eq}$ at the $n^{th}$ equilibrium will be:

$$K_{eq} = \frac{m_{H^+_n}(m_{Y^-_1} - x_1 - x_2 - x_3 \ldots - x_{n-1})}{(m_{HY_1} + x_1 + x_2 + \ldots + x_{n-1})[V_1 + (n-1)V_s]} \qquad (13)$$

Using sum notation, we can write:

$$K_{eq} = \frac{m_{H^+_n}\left(m_{Y^-_1} - \sum_{i=0}^{n-1} x_i\right)}{\left(m_{HY_1} + \sum_{i=0}^{n-1} x_i\right)[V_1 + (n-1)V_s]} \qquad (14)$$

or $$K_{eq}\left(m_{HY_1} + \sum_{i=0}^{n-1} x_i\right)[V_1 + (n-1)V_s] - m_{H^+_n}\left(m_{Y^-_1} - \sum_{i=0}^{n-1} x_i\right) = 0, \qquad (15)$$

$$n = 1, 2, 3 \ldots, x_0 = 0$$

Equation (14) applies to all equilibrium states including the initial equilibrium state where $x_0$=0 (before disturbance). Equation (15) indicates that the number of unknowns (including $K_{eq}$, $m_{HY_1}$, $m_{Y^-_1}$) at successive equilibrium states (denoted by n=1, 2, 3, . . . ) is constant. For instance, the first equilibrium has as many unknowns as the second or third equilibrium. Thus, in reaction (b), to determine three unknowns, it is necessary to disturb the initial equilibrium at least twice, to provide a mathematical system with three equations and three unknowns. Various computer programs can be used to obtain all unknowns in the equation (15). For example, a Microsoft Excel file that contains a number of commands to solve equation (15) is included below.

After the determination of $m_{HY}$ and $m_{Y^-_1}$, using equation (15), the initial number of moles of HY can be calculated with the following formula:

$$m_{HY} = m_{HY_1} + m_{Y^-_1} \qquad (16)$$

Using $m_{HY}$ and the experimentally measured mass of HY, it is possible to calculate the molecular weight of HY with the following formula:

$$M\overline{W}_{HY} = \frac{mass_{HY} \; (g)}{m_{HY} \; (\text{mole})} \qquad (17)$$

Figure 2:
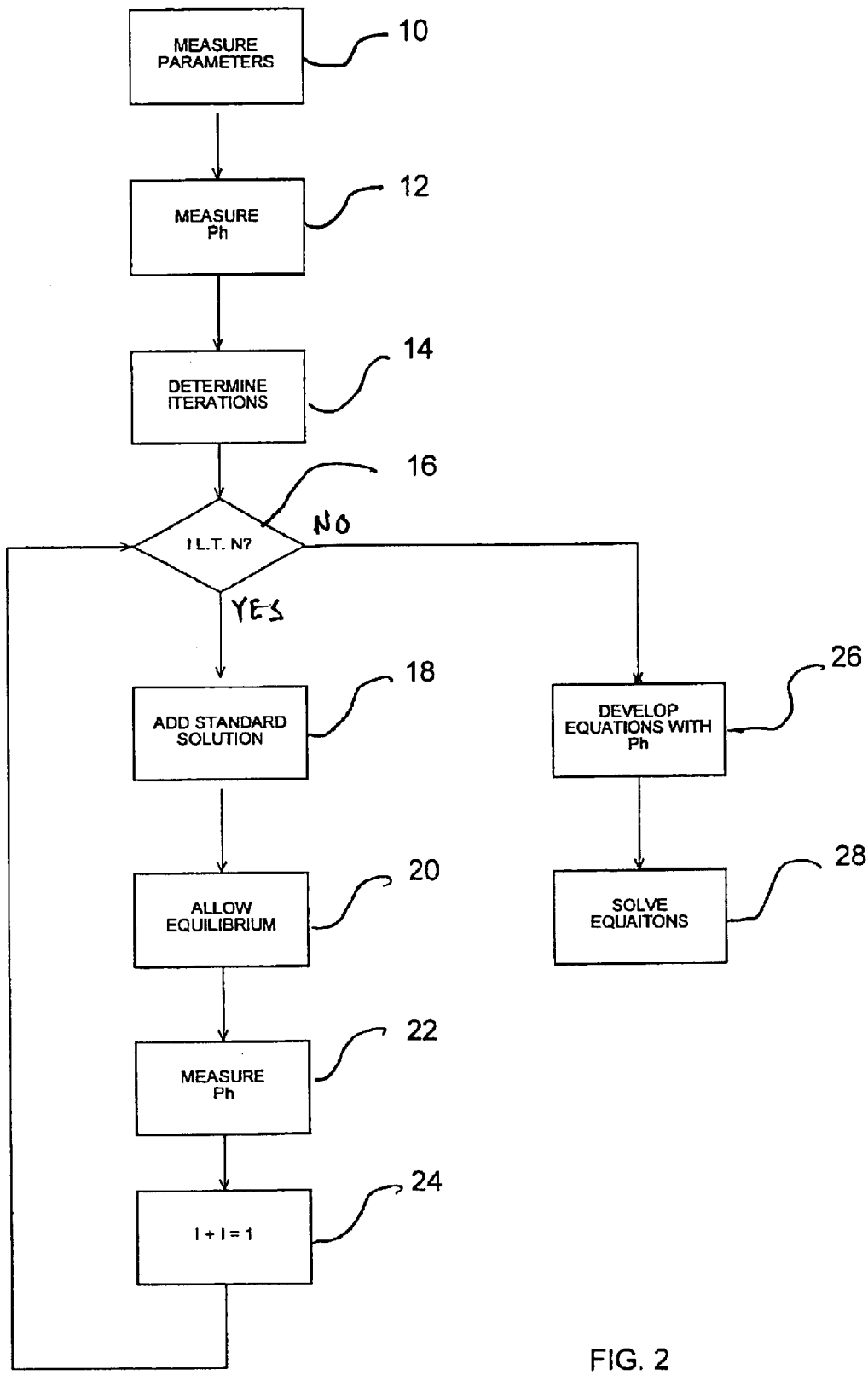
FIG. 2 is a flow chart that illustrates the procedure utilized by the present invention.

The flow chart shown in FIG. 2 illustrates an algorithm that represents the iterative nature of the invention when applied to a test sample. In functional block 10, parameters of the test sample are measured. The measured parameters include the mass and volume of the test sample. The pH of the test sample is measured in functional block 20. The number of iterations is determined in functional block 30. Since there are three unknowns, the test solution is disturbed twice. Thus, the iteration counter, I, is initially set at one and the number of iterations, N, is set at 3. While the minimum number of iterations for the example is three, the invention also may be practiced with additional iterations. The inventors have determined that additional iterations can increase the accuracy of the process. The algorithm then proceeds to decision block 16.

In decision block 16, the iteration counter is compared to the number of iterations. If the iteration counter I is less than the number of iterations N, the algorithm transfers to functional block 18 where a known volume of a standard solution is added to the test sample to yield a modified test sample. The modified test sample is allowed to reach equilibrium in functional block 20 and then the pH of the modified test sample is measured in functional block 22. In functional block 24, the iteration counter I is indexed by one and the algorithm returns to decision block 16.

The process is repeated until the iteration counter I is equal to the number of iterations N in decision block 16, at which time the algorithm transfers to functional block 26. In functional block 26, the measured pH values are used to determine three equations. The equations are solved simultaneously in functional block 28 to determine the molecular weight of the original test sample.

Fulvic acids are rich in carboxylic acid, phenolic, and ketonic groups. Therefore, to verify the validity of the invention, in addition to fulvic acids, the inventors also examined selected compounds with diverse molecular structures. Included in their analysis were aurintricarboxylic acid, having the chemical structure illustrated in FIG. 1A, 2-acetyl benzoic acid, having the chemical structure illustrated in FIG. 1B, and bromocresol green having the chemical structure illustrated in FIG. 1C.

Table 1 below contains the experimental conditions for examining the analytes of the above listed test samples. Less than 2 mg of each analyte was weighed within accuracy of ±0.1 mg (second column of Table 1). The stock solution of each analyte was prepared using deionized water, available from Spectrum, New Brunswick, N.J. The volume of stock solution is given in the third column of Table 1. At a given temperature (the fifth column of Table 1), a specified volume of the standard solution of hydrochloric acid (Fisher Scientific) was successively added to the specified amount of stock solution (the forth column in Table 1). The normality (N) and the volume ($V_s$) of the standard HCl solution used for disturbing the equilibrium conditions are given in the sixth and seventh columns of Table 1, respectively. An accurate pipette from Rainin Instrument Co. Inc. was used to measure the volume of the added acid. After addition of the standard acid (HCl) to disturb each equilibrium state, a sufficient time was allowed for the reaction to reach a new equilibrium state and the pH of the solution was measured using a model 250 pH meter which is available from Denver Instrument in Arvada, Colo. The pH values were recorded once the pH meter readings were stable to within ±0.001 pH unit. Buffer solutions with the pHs 3 and 5 (Fisher Scientific) were used to calibrate the pH meter prior to each experiment.

TABLE 1

Experimental Conditions and Selected Parameters

| Compound | Original Dissolved Mass (mg) | Volume of the Stock Solution (mL) | Volume of Sample/Trial (mL) | T (° C.) | HCl (N) | $V_s$ (µL) |
|---|---|---|---|---|---|---|
| Fulvic Acid | 17.6 ± 0.1 | 100 ± 0.08 | 8 ± 0.1 | 25 ± 1 | 0.05 | 10 ± 0.01 |
| 2-Acetylbenzoic acid | 54.2 ± 0.1 | 500 ± 0.2 | 8 ± 0.1 | 25 ± 1 | 0.05 | 10 ± 0.01 |
| Aurintricarboxylic acid | 34.0 ± 0.1 | 500 ± 0.2 | 8 ± 0.1 | 25 ± 1 | 0.05 | 10 ± 0.01 |
| Bromocresol green (water soluble) | 724 ± 11 | 100 ± 0.08 | 8 ± 0.1 | 25 ± 1 | 0.05 | 20 ± 0.01 |

For the reaction (b), there are three unknowns at the equilibrium state, namely, $K_a$, $[HY]_1$, $[Y^-]_1$ and, as described above, it is necessary to disturb the reaction equilibrium at least twice. To reduce the experimental errors, the acid dissociation systems were disturbed six times. The observed pHs of the examined analytes (for the selected trials) at the $n_{th}$ equilibrium states, e.g., from $pH_1$ to $pH_7$, are given in Table 2 below.

TABLE 2

PHns Observed at Successive Equilibrium States for the Analytes Examined

| | Pulvic Acids | 2-Acetyl benzoic acid | Aurintricarboxylic acid | Bromocresol Green |
|---|---|---|---|---|
| pH1 | 3.649 | 3.718 | 3.862 | 4.747 |
| pH2 | 3.492 | 3.639 | 3.729 | 4.666 |
| pH3 | 3.372 | 3.566 | 3.622 | 4.582 |
| pH4 | 3.274 | 3.500 | 3.534 | 4.498 |
| pH5 | 3.194 | 3.438 | 3.459 | 4.413 |
| pH6 | 3.125 | 3.383 | 3.395 | 4.327 |
| pH7 | 3.065 | 3.332 | 3.337 | 4.240 |

There are different possible sets of equilibrium states that can be used to establish three equations with three unknowns. For example, it is possible to consider the three equilibrium states ($pH_1$, $pH_2$, $pH_3$) or ($pH_2$, $pH_3$, $pH_5$), etc. Therefore there are 35 possible sets of answers for the unknown parameters and an average value can be acquired. Using Eqs. (15–17), and the explemarly Microsoft Excel program that is listed below, average values of $K_{eq}$, $m_{HY1}$, $m_{Y^-1}$ were obtained and the molecular weight were obtained for the analytes examined.

The following Table 3 indicates the calculated molecular weights and the corresponding errors for the tested samples. As an example, the results for one of the trials of Fulvic acids acquired from the equations (15–17) and Microsoft Excel commands are discussed in detail below.

TABLE 3

Experimentally Calculated and Actual Molecular Weights

| Compound | Experimentally Calculated Molecular Weight (Da) (Tests with invention) | Actual Molecular Weight (Da) | % Relative Error |
|---|---|---|---|
| Fulvic Acid | 551 ± 10 | Not determined | — |
| 2-Acetylbenzoic acid | 163 ± 3 | 164.12 | 0.61 |
| Aurintricarboxylic acid | 425 ± 10 | 422.35 | 0.68 |
| Bromocresol green (water soluble) | 724 ± 11 | 720.02 | 0.55 |

Because the pH is −log[H+], the inventors have determined that, to reduce experimental errors, it is critical that the pH is measured as accurately as possible. There are some additional sources of experimental error and it also is important to minimize these contributions. For example, only at a constant temperature, the equilibrium constant will remain unchanged at different equilibrium states re-established after consecutive disturbances; hence, during the experiment, temperature of the system must be kept constant. The volume of the added species, i.e., $V_s$, should be measured as accurately as possible. The measuring device, e.g., pH meter, must be calibrated before each trail. The solution should be as dilute as possible so that in the relation $K_{eq}=K_\gamma K_c$, we can assume: $K_\gamma \rightarrow 1$, $K_{eq} \equiv K_c$ and $a_j \equiv [j]$, where $a_j$ and $[j]$ are activity and molar concentration of the species j, respectively, $K_\gamma$ is activity coefficient-based equilibrium constant, and $K_c$ is molar concentration-based equilibrium constant. The pH of the solvent must be checked prior to disturbing the system to ensure that no other acidic compounds are present in the system; otherwise, due to the chemical interference, the system under investigation will not be governed by the reaction (b).

Table 4 below indicates the mass range and/or average molecular weights (Da) of Suwannee River fulvic acid sample obtained by using various techniques including the approach described above.

TABLE 4

Comparison of results

| ESI FT-ICR MS | LD FT-ICR MS | GFC | VPO | Result with Invention |
|---|---|---|---|---|
| 200–1700 | 200–800 | 960 | 829* | 551 ± 10 |

*Consideration of the dissociation degree (α) acquired in this test yields the corrected value of 509 Da for Suwannee River fulvic acid.

In an article published in Science Technology, 29 (1995) 399, J. A. Leenheer et al. proposed three "structural models" for fulvic acid molecules from the Suwannee River. The molecular weights of these "structural models" are 566, 688, and 774 Da. The average molecular weight of the Suwannee River fulvic acid calculated in the above described test (551±10 Da) agrees with the molecular weight of one of the structural models suggested by Leenheer et al. The average molecular weight obtained in the above test is in the mass range acquired from LD FT-ICR MS and ESI ICR-FT MS. ESI FT-ICR mass spectrum shows ions in the mass range of 200–1700 Da. It is not clear that high-mass ions obtained from ESI FT-ICR MS are intact species or due to aggregation. For fulvic acid samples, ESI FT-ICR MS has also been utilized to study the number of active hydrogens, and the binding sites upon metal complexation reactions. For example, northern hardwood and red spruce fulvic acid samples contain at least 7active hydrogens at the mass region 700–1000 Da. In contrast to LD FT-ICR MS and ESI ICR-FT MS, using the method described above, the average molecular weight of fulvic acids was measured directly from the solution phase and fragmentation and aggregation are not major issues.

It is known in the prior art that the unknown extent of dissociation degree (α) of fulvic acids has been a major problem in determining the molecular weight of fulvic acids by vapor pressure osmometry. Prior art studies using vapor pressure osmometry (VPO) and complementary calculations have reported the dissociation-corrected average molecular weights of fulvic acid samples, e.g., 643, and 633 Da for soil fulvic acid and water fulvic acid, respectively. The prior art studies utilized the dissociation constant obtained from the titration of fulvic acid sample in the pH range of 1.6 to 2.

With the present invention, the average molecular weight of fulvic acid is determined considering the dissociation reaction (a) and hence the extent of dissociation is considered. Furthermore, the dissociation constant as well as the average molecular weight of Suwannee River fulvic acid is simultaneously acquired (see Eq. 15); therefore, the dissociation degree α can be calculated and thus correct the reported Average Molecular Weight (AMW) of Suwannee River fulvic acid samples obtained from VPO.

For example, using the calculated average pKa and AMW for Suwannee River fulvic acid obtained from this study (3.34±0.04 and 551±10 Da, respectively), the dissociation degree α is calculated to be 63% for Suwannee River fulvic acid. This number can be used to calculate the estimated number of moles (1±α=1.63) of particles present in the solution. Recalculation of the previously reported AMW obtained from VPO (829 Da, see Table 3) yields an AMW of 509 Da for Suwannee River fulvic acid. It should be noted that the reported AMW of 829 Da is the result of a duplicate experiment and the AMW reported in herein (510±10) was obtained using 10 trials.

To verify the validity of the new approach, the inventors analyzed different compounds with a variety of functional groups such as carboxylic acid, alcoholic, and carbonly groups. It was assumed that, for multiprotic acids (such as aurintricarboxylic acid), only the first dissociation reaction should be considered. For the compounds analyzed, the system was disturbed by adding a small amount of standard acid, which prevented the second and next dissociation reactions due to the common ion effect. The experimentally calculated molecular weights (Table 3) and theoretical values were in good agreement (within <1%). The average molecular weight calculated for Suwannee River fulvic acid was tested by calculating the measured mass of analyte (in grams) and comparing it to the experimental value (value obtained from the analytical balance). For example, using Eqs. (15–17) and the average molecular weight obtained, the inventors predicted the mass of Suwannee River fulvic acid present in a number of samples within an average relative error of 6.5 percent.

To summarize the above tests, successive disturbances of a reaction at equilibrium were used to calculate the average molecular weight of the Suwannee River fulvic acid sample. The calculated value was (551±10 Da). To verify the process of the invention, three additional compounds with different structures and functional groups and known molecular weights were utilized. The calculated molecular weights for the compounds examined including 2-acetyl benzoic acid, aurintricarboxylic acid, and bromocresol green are 163±3, 425±10, 724±11 Da, respectively. These numbers are in good agreement with the actual molecular weights of these species (164.12, 422.35, 720.02 Da, respectively).

The process described above is general and may be used to determine the molecular weight of a variety of environmental and biological macromolecules. For example, the inventors also contemplate that the invention can be utilized to determine the stoichiometery, $pK_a$ and molar concentrations of macromolecules in solution. Thus, while the preferred embodiment of the invention has been described and illustrated for the determination of the AMW fulvic acids in a solution, it will be appreciated that the invention also can be utilized to determine the stoichiometry, $pK_a$ and molar concentrations of a solution. Indeed, the simultaneous solution of the equations will yield several parameters, as demonstrated in the example presented below.

Furthermore, while the preferred embodiment is described for developing simultaneous equations by adding increments of an acidic solution to change the pH of an aqueous solution, it also will be appreciated that the invention also can be practiced by adding increments of an alkaline solution to change the pH of an aqueous solution in the opposite direction.

Additionally, the invention also contemplates measuring other parameters of a solution instead of the pH to determine unknown equilibria parameters. For example, some viruses may not be appropriate for acid-base studies, but may react with metals, such as copper. Accordingly, the invention contemplates adding predetermined amounts of a metal contained in a standard solution and then monitoring the pmetal, such as, for example pCu, of the resulting solution once equilibrium is re-established. For example, a solution containing copper can be added and the pCu measured. The process would be repeated and a set of equations determined that would then be solved for an unknown equilibria parameter.

As described above, the invention contemplates a simple program containing a series of Microsoft Excel commands to solve the mathematical system with three equations and three unknowns (derived from Eq. 15). Details of an exemplary procedure are given in Tables 5 and 6 below. The first portion of the program, which is included in Table 5, includes data arranged in two parts designated as "Input" and "Output". For convienence, the data in Table 5 is referred to in the following in terms of "Cells" which are identified with a column letter and row number.

To calculate the unknowns, one only needs to enter the primary known data in the Input section. These data include the measured mass (mg) of the sample used for preparing stock solution (Cell F6), the volume (mL) of stock solution (Cell F7), the initial volume of trial in liter (Cell F9), the concentration (Normality) and volume (in microliter) of the standard acid added to disturb the equilibrium (Cells F10 and F11, respectively), and the observed $pH_n$'s for equilibrium states after successive disturbances of the initial equilibrium (Cells H6–H11). If the molecular weight is known, the mass of the sample can be determined; in this case, the molecular weight of the species is entered in Cell F12. Cells (I6–I12) represent the trend of change in the pH of the solution after each disturbance. Cells E16–M16 show the results of calculation. A maximum of 35 sets of answers for each parameter (indicated in the Cell rows 16–50 for each parameter) can be acquired. For example, the 25th row in Table 5 indicates the parameters calculated using the set including the three equilibrium states $pH_1$, $pH_4$, and $pH_5$.

It should be noted that before taking the average of results acquired, some of the calculated results might be statistically rejected. For instance, for the selected data shown in Table 5, the results from the rows 41 and 47 were rejected.

TABLE 5

| | B | C | D | E | F | G | H | I | J | K | L | M | N |
|---|---|---|---|---|---|---|---|---|---|---|---|---|---|
| 2 | | | | | | | Data | | | | | | |
| 3 | | | | | | | Input | | | | | | |
| 4 | | | | Compound: Fulvic Acids | | | | | | | | | |
| 5 | | | | Puffy | 100% | | | | | | | | |
| 6 | | | | Temperature (° C.) | 25 | | | | | | | | |
| 7 | | | | Measured mass of stock sample (mg) | 17.8 | | | | | | | | |
| 8 | | | | Volume of stock solution (mL) | 100 | | | | | | | | |
| 9 | | | | Measured mass/trail (g) | 0.0014 | | | | | | | | |
| 10 | | | | Initial volume of trial (L) | 0.008 | | | | | | | | |
| 11 | | | | Concentration of HCl (M) | 0.05 | | | | | | | | |
| 12 | | | | Volume of HCl added (uL) | 20 | | pH$_n$ | 3.649 | pH$_n$ · pH$_{n-1}$ | | | | |
| | | | | Molecular weight | 549 | | pH$_1$ | 3.492 | 0.157 | | | | |
| | | | | | | | pH$_2$ | 3.372 | 0.12 | | | | |
| | | | | | | | pH$_3$ | 3.274 | 0.098 | | | | |
| | | | | | | | pH$_4$ | 3.194 | 0.08 | | | | |
| | | | | | | | pH$_5$ | 3.125 | 0.069 | | | | |
| | | | | | | | pH$_6$ | 3.065 | 0.06 | | | | |
| | | | | | | | pH$_7$ | | | | | | |
| 13 | | | | | | | Output | | | | | | |
| 14 | | | | | | | | | | | | | |
| 15 | The three pH$_n$s selected for Eq. (15) | | | K$_s$ | m$_{NT_1}$ | m$_{T_1}$ | (HY)$_1$ | [Y"]$_1$ | [HY]$_o$ | pK$_a$ | Mass (g) | Molecular Weight |
| 16 | 1 | 2 | 3 | 0.000417323 | 8.618E-07 | 1.603E-06 | 0.000108 | 0.0002 | 0.000308 | 3.37953 | 0.0013518 | 589.8297805 |
| 17 | 1 | 2 | 4 | 0.000339821 | 9.477E-07 | 1.434E-06 | 0.000118 | 0.000179 | 0.000296 | 3.48901 | 0.0013065 | 589.5741683 |
| 18 | 1 | 2 | 5 | 0.000403018 | 8.751E-07 | 1.572E-06 | 0.000109 | 0.000196 | 0.000306 | 3.39468 | 0.0013421 | 573.9475855 |
| 19 | 1 | 2 | 6 | 0.00041558 | 8.633E-07 | 1.588E-06 | 0.000108 | 0.0002 | 0.000306 | 3.38135 | 0.0013506 | 570.3396775 |
| 20 | 1 | 2 | 7 | 0.000429902 | 8.508E-07 | 1.83E-08 | 0.000106 | 0.000204 | 0.00031 | 3.36883 | 0.0013607 | 566.0902324 |
| 21 | 1 | 3 | 4 | 0.000280214 | 1.124E-06 | 1.304E-06 | 0.000141 | 0.000163 | 0.000303 | 3.58467 | 0.0013317 | 578.4358519 |
| 22 | 1 | 3 | 5 | 0.000395493 | 6.881E-07 | 1.557E-06 | 0.000111 | 0.000195 | 0.000306 | 3.40508 | 0.0013414 | 574.2870798 |
| 23 | 1 | 3 | 6 | 0.000414715 | 8.645E-07 | 1.598E-06 | 0.000108 | 0.0002 | 0.000306 | 3.38225 | 0.0013506 | 570.3461857 |
| 24 | 1 | 3 | 7 | 0.000435061 | 8.44E-07 | 1.637E-06 | 0.000108 | 0.000205 | 0.00031 | 3.38143 | 0.0013608 | 568.1393447 |
| 25 | 1 | 4 | 5 | 0.000842766 | 6.748E-07 | 1.933E-06 | 8.44E-05 | 0.000242 | 0.0003226 | 3.19195 | 0.0014035 | 538.4890083 |
| 26 | 1 | 4 | 6 | 0.000560639 | 7.196E-07 | 1.798E-06 | 9E-05 | 0.000225 | 0.000315 | 3.25132 | 0.0013809 | 557.8154608 |
| 27 | 1 | 4 | 7 | 0.00055309 | 7.244E-07 | 1.786E-06 | 9.05E-05 | 0.000223 | 0.000314 | 3.2572 | 0.0013767 | 559.5130968 |
| 28 | 1 | 5 | 8 | 0.000476856 | 7.52E-07 | 1.683E-06 | 9.9E-05 | 0.00021 | 0.000309 | 3.32161 | 0.0013675 | 587.4182108 |
| 29 | 1 | 5 | 7 | 0.000502467 | 7.688E-07 | 1.722E-06 | 9.61E-05 | 0.000215 | 0.000311 | 3.29889 | 0.001366 | 583.8905317 |
| 30 | 1 | 6 | 7 | 0.000534195 | 7.4E-07 | 1.762E-06 | 0.25E-05 | 0.00022 | 0.000313 | 3.2723 | 0.0013722 | 581.3699679 |
| 31 | 2 | 3 | 4 | 0.000766831 | 1.581E-06 | 1.209E-06 | 0.000224 | 0.00022 | 0.000444 | 3.1163 | 0.0015307 | 503.2268067 |
| 32 | 2 | 3 | 5 | 0.000179181 | 9.121E-07 | 1.544E-06 | 0.00014 | 0.000125 | 0.000266 | 3.74671 | 0.0013472 | 571.7570906 |
| 33 | 2 | 3 | 6 | 0.000381822 | 8.668E-07 | 1.597E-06 | 0.000135 | 0.000167 | 0.000301 | 3.41814 | 0.0013511 | 570.1224788 |
| 34 | 2 | 3 | 7 | 0.000413635 | 8.32E-07 | 1.643E-06 | 0.00013 | 0.000173 | 0.000304 | 3.38338 | 0.0013575 | 587.4488178 |
| 35 | 2 | 4 | 5 | 0.000441617 | 5.078E-07 | 2.216E-06 | 5E-05 | 0.000179 | 0.000289 | 3.35495 | 0.001494 | 515.6041755 |
| 36 | 2 | 4 | 6 | 0.000896853 | 5.665E-07 | 1.925E-06 | 0.0001 | 0.00025 | 0.000351 | 3.04726 | 0.0013787 | 558.7248272 |
| 37 | 2 | 4 | 7 | 0.000689484 | 6.058E-07 | 1.88E-06 | 0.000102 | 0.000214 | 0.000316 | 3.16148 | 0.0013633 | 565.0351983 |
| 38 | 2 | 5 | 6 | 0.000667294 | 7.344E-07 | 1.712E-06 | 0.000118 | 0.000209 | 0.000327 | 3.18224 | 0.001342 | 573.9831483 |
| 39 | 2 | 5 | 7 | 0.000510748 | 7.034E-07 | 1.754E-06 | 0.000114 | 0.000188 | 0.000302 | 3.29179 | 0.0013479 | 571.4751909 |
| 40 | 2 | 6 | 7 | 0.000542816 | 6.649E-07 | 1.798E-06 | 0.00011 | 0.000193 | 0.000302 | 3.26535 | 0.0013509 | 5702218244 |
| 41 | 3 | 4 | 5 | 0.00076617 | 1.759E-07 | 5.886E-06 | 6.96E-05 | 0.000198 | 0.000268 | 3.11454 | 0.0033251 | 231.8582102 |
| 42 | 3 | 4 | 6 | 0.004196139 | 3.053E-07 | 2.595E-06 | 8.68E-05 | 0.000688 | 0.000774 | 2.37716 | 0.0015909 | 484.188596 |
| 43 | 3 | 4 | 7 | 0.001369411 | 3.533E-07 | 2.276E-06 | 9.18E-05 | 0.00277 | 0.000369 | 2.86347 | 0.0014424 | 534.027182 |
| 44 | 3 | 5 | 6 | 0.00109571 | 6.282E-07 | 1.779E-06 | 0.000126 | 0.000237 | 0.000363 | 2.9603 | 0.0013202 | 583.4635849 |

TABLE 5-continued

| | A | B | C | D | E | F | G | H | I | J | K | L | M | N |
|---|---|---|---|---|---|---|---|---|---|---|---|---|---|---|
| | | | | | | | | Data | | | | | | |
| 45 | 3 | | 5 | 7 | | 0.000687973 | 5.99E−087 | 1.818E−06 | 0.000123 | 0.000297 | 3.23064 | 0.0013268 | 581.015396 | |
| 46 | 3 | | 6 | 7 | | 0.000622523 | 5.625E−07 | 1.859E−06 | 0.000116 | 0.000298 | 3.20584 | 0.0013284 | 579.8575204 | |
| 47 | 4 | | 5 | 6 | | 0.000833472 | 1.841E−06 | 1.333E−06 | 0.000293 | 0.000478 | 3.07911 | 0.0017407 | 442.522216 | |
| 48 | 4 | | 5 | 7 | | 0.000216799 | 1.257E−06 | 1.578E−06 | 0.00022 | 0.000339 | 3.68595 | 0.001555 | 495.3863481 | |
| 49 | 4 | | 6 | 7 | | 0.000323202 | 8.182E−07 | 1.73E−06 | 0.000156 | 0.000299 | 3.49053 | 0.0013976 | 551.1401602 | |
| 50 | 5 | | 6 | 7 | | 0.00059099 | 4.50E−07 | 1.95E−06 | 0.000135 | 0.000287 | 3.22842 | 0.0013168 | 584.9868903 | |
| 51 | | | | | | | | | | | | | | |
| 52 | B | | | | $V_a$ | $pH_0$ | $pH_1$ | $pH_2$ | $V_0$ | $V_1$ | $V_2$ | $m_a$ | $m_{A0}$ | |
| 53 | The three $pH_n$s selected for Eq. (15) | | | | | | | | | | | | | |
| 54 | 1 | | 2 | 3 | 20 | 3.649 | 3.492 | 3.372 | 0.008 | 0.00802 | 0.00804 | 0.000001 | 1.79511E−06 | |
| 55 | 1 | | 2 | 4 | 20 | 3.649 | 3.492 | 3.274 | 0.008 | 0.00802 | 0.00806 | 0.000001 | 1.79511E−06 | |
| 56 | 1 | | 2 | 5 | 20 | 3.649 | 3.492 | 3.194 | 0.008 | 0.00802 | 0.00806 | 0.000001 | 1.79511E−06 | |
| 57 | 1 | | 2 | 6 | 20 | 3.649 | 3.492 | 3.125 | 0.008 | 0.00802 | 0.0081 | 0.000001 | 1.79511E−06 | |
| 58 | 1 | | 2 | 7 | 20 | 3.649 | 3.492 | 3.065 | 0.008 | 0.00802 | 0.00812 | 0.000001 | 1.79511E−06 | |
| 59 | 1 | | 3 | 4 | 20 | 3.649 | 3.372 | 3.274 | 0.008 | 0.00802 | 0.00806 | 0.000001 | 1.79511E−06 | |
| 60 | 1 | | 3 | 5 | 20 | 3.649 | 3.372 | 3.194 | 0.008 | 0.00802 | 0.00808 | 0.000001 | 1.79511E−06 | |
| 61 | 1 | | 3 | 6 | 20 | 3.649 | 3.372 | 3.125 | 0.008 | 0.00804 | 0.00808 | 0.000001 | 1.79511E−06 | |
| 62 | 1 | | 3 | 7 | 20 | 3.649 | 3.372 | 3.065 | 0.008 | 0.00804 | 0.0081 | 0.000001 | 1.79511E−06 | |
| 63 | 1 | | 4 | 5 | 20 | 3.649 | 3.274 | 3.194 | 0.008 | 0.00804 | 0.00808 | 0.000001 | 1.79511E−06 | |
| 64 | 1 | | 4 | 6 | 20 | 3.649 | 3.274 | 3.125 | 0.008 | 0.00804 | 0.00808 | 0.000001 | 1.79511E−06 | |
| 65 | 1 | | 4 | 7 | 20 | 3.649 | 3.274 | 3.065 | 0.008 | 0.00806 | 0.0081 | 0.000001 | 1.79511E−06 | |
| 66 | 1 | | 5 | 6 | 20 | 3.649 | 3.194 | 3.125 | 0.008 | 0.00806 | 0.00812 | 0.000001 | 1.79511E−06 | |
| 67 | 1 | | 5 | 7 | 20 | 3.649 | 3.194 | 3.065 | 0.008 | 0.00806 | 0.00812 | 0.000001 | 1.79511E−06 | |
| 68 | 1 | | 6 | 7 | 20 | 3.649 | 3.125 | 3.065 | 0.008 | 0.0081 | 0.0081 | 0.000001 | 1.79511E−06 | |
| 69 | 2 | | 3 | 4 | 20 | 3.492 | 3.372 | 3.274 | 0.00802 | 0.00804 | 0.00806 | 0.000001 | 2.5833E−06 | |
| 70 | 2 | | 3 | 5 | 20 | 3.492 | 3.372 | 3.194 | 0.00802 | 0.00804 | 0.00808 | 0.000001 | 2.5833E−06 | |
| 71 | 2 | | 3 | 6 | 20 | 3.492 | 3.372 | 3.125 | 0.00802 | 0.00804 | 0.00808 | 0.000001 | 2.5833E−06 | |
| 72 | 2 | | 3 | 7 | 20 | 3.492 | 3.372 | 3.065 | 0.00802 | 0.00804 | 0.0081 | 0.000001 | 2.5833E−06 | |
| 73 | 2 | | 4 | 5 | 20 | 3.492 | 3.274 | 3.194 | 0.00802 | 0.00806 | 0.00808 | 0.000001 | 2.5833E−06 | |
| 74 | 2 | | 4 | 6 | 20 | 3.492 | 3.274 | 3.125 | 0.00802 | 0.00806 | 0.0081 | 0.000001 | 2.5833E−06 | |
| 75 | 2 | | 4 | 7 | 20 | 3.492 | 3.274 | 3.065 | 0.00802 | 0.00806 | 0.00812 | 0.000001 | 2.5833E−06 | |
| 76 | 2 | | 5 | 6 | 20 | 3.492 | 3.194 | 3.125 | 0.00802 | 0.00808 | 0.00812 | 0.000001 | 2.5833E−06 | |
| 77 | 2 | | 5 | 7 | 20 | 3.492 | 3.194 | 3.065 | 0.00802 | 0.00808 | 0.00812 | 0.000001 | 2.5833E−06 | |
| 78 | 2 | | 6 | 7 | 20 | 3.492 | 3.125 | 3.065 | 0.00804 | 0.0081 | 0.0081 | 0.000001 | 2.5833E−06 | |
| 79 | 3 | | 4 | 5 | 20 | 3.372 | 3.274 | 3.194 | 0.00804 | 0.00806 | 0.00808 | 0.000001 | 3.41394E−06 | |
| 80 | 3 | | 4 | 6 | 20 | 3.372 | 3.274 | 3.125 | 0.00804 | 0.00806 | 0.00812 | 0.000001 | 3.41394E−06 | |
| 81 | 3 | | 4 | 7 | 20 | 3.372 | 3.274 | 3.065 | 0.00804 | 0.00808 | 0.00812 | 0.000001 | 3.41394E−06 | |
| 82 | 3 | | 5 | 6 | 20 | 3.372 | 3.194 | 3.125 | 0.00804 | 0.00808 | 0.00812 | 0.000001 | 3.41394E−06 | |
| 83 | 3 | | 5 | 7 | 20 | 3.372 | 3.194 | 3.065 | 0.00806 | 0.00808 | 0.0081 | 0.000001 | 3.41394E−06 | |
| 84 | 3 | | 6 | 7 | 20 | 3.372 | 3.125 | 3.065 | 0.00806 | 0.0081 | 0.0081 | 0.000001 | 3.41394E−06 | |
| 85 | 4 | | 5 | 6 | 20 | 3.274 | 3.194 | 3.125 | 0.00806 | 0.00808 | 0.0081 | 0.000001 | 4.28879E−06 | |
| 86 | 4 | | 5 | 7 | 20 | 3.274 | 3.194 | 3.065 | 0.00806 | 0.00808 | 0.00812 | 0.000001 | 4.28879E−06 | |
| 87 | 4 | | 6 | 7 | 20 | 3.274 | 3.125 | 3.065 | 0.00806 | 0.0081 | 0.00812 | 0.000001 | 4.28879 E−06 | |
| 88 | 5 | | 6 | 7 | 20 | 3.194 | 3.125 | 3.065 | 0.00806 | 0.0081 | 0.00812 | 0.000001 | 5.16906E−06 | |

TABLE 5-continued

| | $m_{A1}$ | $m_{A2}$ | X1 | X2 | Y | $a_1$ | $a_2$ | $a_3$ | $a_4$ | $a_5$ | $a_6$ | $m_{nY}$ | $m_Y$ |
|---|---|---|---|---|---|---|---|---|---|---|---|---|---|
| 89 | | | | | | | | | | | | | |
| 90 | | | | | | | | | | | | | |
| 91 | 2.583E-06 | 3.414E-06 | 2.11808E-07 | 1.69358E-07 | 5.612E-27 | 3.968E-27 | 3.01E-27 | 7.9E-21 | 1.49E-20 | 2.7E-20 | 1.873E-20 | 8.81787E-07 | 1.60274E-06 |
| 92 | 2.583E-06 | 4.289E-06 | 2.11808E-07 | 2.94505E-07 | 5.063E-07 | 6.622E-27 | 4.01E-27 | 7.92E-21 | 1.88E-20 | 4.5E-20 | 3.126E-20 | 9.47666E-07 | 1.43432E-06 |
| 93 | 2.583E-08 | 5.169E-06 | 2.11808E-07 | 4.1424E-07 | 6.28E-07 | 9.888E-27 | 4.97E-27 | 7.94E-21 | 2.26E-20 | 6.7E-20 | 4.659E-20 | 8.75092E-07 | 1.57173E-06 |
| 94 | 2.583E-06 | 6.074E-06 | 2.11808E-07 | 5.09154E-07 | 7.21E-07 | 1.335E-06 | 5.74E-27 | 7.96E-21 | 2.68E-20 | 9.1E-20 | 8.305E-20 | 8.63342E-07 | 1.59896E-06 |
| 95 | 2.583E-06 | 6.991E-06 | 2.11808E-07 | 5.92028E-07 | 8.038E-07 | 1.714E-26 | 6.41E-27 | 7.98E-21 | 3.06E-20 | 1.2E-19 | 8.091E-20 | 8.50784E-07 | 1.63E-06 |
| 96 | 3.414E-06 | 4.289E-06 | 3.81164E-07 | 1.25149E-07 | 5.063E-07 | 1.195E-26 | 9.53E-27 | 1.88E-20 | 4.48E-20 | 5.9E-20 | 3.134E-20 | 1.12418E-08 | 1.30366E-06 |
| 97 | 3.414E-06 | 5.169E-06 | 3.81164E-07 | 2.44884E-07 | 6.26E-07 | 1.78E-26 | 1.18E-26 | 1.88E-20 | 5.38E-20 | 8.8E-20 | 4.671E-20 | 8.68066E-07 | 1.55737E-06 |
| 98 | 3.414E-06 | 6.074E-06 | 3.81164E-07 | 3.39798E-07 | 7.21E-07 | 2.409E-26 | 1.36E-26 | 1.89E-20 | 6.32E-20 | 1.2E-19 | 6.32E-20 | 8.64501E-07 | 1.59777E-06 |
| 99 | 3.414E-06 | 6.991E-06 | 3.81164E-07 | 4.22572E-07 | 8.038E-07 | 3.092E-26 | 1.52E-26 | 1.9E-20 | 7.28E-20 | 1.5E-19 | 8.11E-20 | 8.44029E-07 | 1.83654E-06 |
| 100 | 4.289E-06 | 5.169E-06 | 5.06313E-07 | 1.19735E-07 | 6.26E-07 | 2.371E-26 | 1.97E-26 | 3.15E-26 | 8.98E-20 | 1.1E-19 | 4.682E-20 | 6.74841E-07 | 1.9931E-08 |
| 101 | 4.289E-06 | 6.074E-06 | 5.06313E-07 | 2.14649E-07 | 7.21E-07 | 3.208E-26 | 2.28E-26 | 3.16E-26 | 1.06E-19 | 1.5E-19 | 5.336E-20 | 7.18614E-07 | 1.79797E-08 |
| 102 | 4.289E-06 | 6.991E-06 | 5.06313E-07 | 2.97523E-07 | 8.038E-07 | 4.117E-26 | 2.54E-26 | 3.17E-26 | 1.21E-19 | 1.9E-19 | 8.131E-20 | 7.24397E-07 | 1.78555E-06 |
| 103 | 5.169E-06 | 6.074E-06 | 6.26048E-07 | 9.49144E-08 | 7.21E-07 | 3.977E-26 | 3.39E-26 | 4.71E-26 | 1.57E-19 | 1.8E-19 | 6.352E-20 | 7.91959E-07 | 1.68303E-06 |
| 104 | 5.169E-06 | 6.991E-06 | 6.26048E-07 | 1.777788E-07 | 8.038E-07 | 5.103E-26 | 3.79E-26 | 4.72E-26 | 1.81E-19 | 2.3E-19 | 8.151E-20 | 7.68834E-07 | 1.721663E-06 |
| 105 | 6.074E-06 | 8.991E-06 | 7.20962E-07 | 8.28738E-06 | 8.038E-07 | 5.891E-26 | 5.13E-26 | 6.38E-26 | 2.45E-19 | 2.7E-19 | 8.171E-20 | 7.39998E-07 | 1.76169E-06 |
| 106 | 3.414E-06 | 4.289E-06 | 1.69355E-07 | 1.25149E-07 | 2.945E-07 | 4.443E-26 | 3.55E-27 | 1.2E-20 | 1.99E-20 | 3.5E-20 | 2.623E-20 | 1.79318E-06 | 9.97508E-07 |
| 107 | 3.414E-06 | 5.169E-06 | 1.69356E-07 | 2.448884E-07 | 4.142E-07 | 7.532E-27 | 5E-27 | 1.21E-20 | 2.4E-20 | 5.9E-20 | 4.447E-20 | 1.12392E-06 | 1.33226E-06 |
| 108 | 3.414E-06 | 6.074E-06 | 1.693585E-07 | 3.39798E-07 | 5.092E-07 | 1.088E-26 | 8.16E-27 | 1.21E-20 | 2.82E-20 | 8.5E-20 | 8.423E-20 | 1.0784E-06 | 1.38464E-06 |
| 109 | 3.414E-06 | 6.991E-06 | 1.69356E-07 | 4.22672E-07 | 5.92E-07 | 1.458E-26 | 7.18E-27 | 1.21E-20 | 3.24E-19 | 1.1E-19 | 8.597E-20 | 1.04379E-06 | 1.43108E-06 |
| 110 | 4.289E-06 | 5.169E-06 | 2.94505E-07 | 1.19735E-07 | 4.142E-07 | 1.313E-26 | 1.09E-26 | 2.64E-26 | 5.24E-20 | 7.4E-20 | 4.458E-20 | 7.19729E-07 | 2.00397E-06 |
| 111 | 4.289E-06 | 6.074E-06 | 2.94505E-07 | 2.14849E-07 | 5.092E-07 | 1.896E-26 | 1.36E-26 | 2.64E-26 | 6.15E-20 | 1.1E-19 | 8.439E-20 | 8.00335E-07 | 1.71315E-06 |
| 112 | 4.289E-06 | 6.991E-06 | 2.94505E-07 | 2.97523E-07 | 5.92E-07 | 2.538E-26 | 1.57E-28 | 2.65E-26 | 7.08E-20 | 1.4E-19 | 8.618E-20 | 8.17409E-07 | 1.88801E-06 |
| 113 | 5.169E-06 | 6.074E-06 | 4.1424E-07 | 9.49144E-08 | 5.092E-07 | 2.674E-26 | 2.28E-26 | 4.48E-26 | 1.04E-19 | 1.3E-19 | 8.458E-20 | 9.46251E-07 | 1.50042E-06 |
| 114 | 5.169E-06 | 6.991E-06 | 4.1424E-07 | 1.777788E-07 | 5.92E-07 | 3.579E-26 | 2.66E-26 | 4.49E-26 | 1.2E-19 | 1.7E-19 | 8.839E-20 | 9.15166E-07 | 1.54224E-06 |
| 115 | 6.074E-06 | 6.991E-06 | 5.09154E-07 | 8.28738E-08 | 5.92E-07 | 4.41E-26 | 3.84E-26 | 6.49E-26 | 1.73E-19 | 2E-19 | 8.661E-20 | 8.76733E-07 | 1.58608E-06 |
| 116 | 4.289E-06 | 5.169E-06 | 1.25149E-07 | 1.19735E-07 | 2.449E-07 | 4.359E-27 | 3.83E-27 | 1.48E-26 | 2.23E-20 | 4.4E-20 | 3.483E-20 | 5.57075E-07 | 6.50508E-06 |
| 117 | 4.289E-06 | 6.074E-06 | 1.25149E-07 | 2.14849E-07 | 3.398E-07 | 7.108E-27 | 5.04E-27 | 1.48E-26 | 2.82E-20 | 7.1E-20 | 5.679E-20 | 6.86484E-07 | 2.21393E-06 |
| 118 | 4.289E-06 | 6.991E-06 | 1.25149E-07 | 2.97523E-07 | 4.227E-07 | 1.018E-28 | 8.29E-27 | 1.49E-26 | 3.02E-20 | 1E-19 | 8.131E-20 | 7.3447E-07 | 1.69526E-06 |
| 119 | 5.169E-06 | 6.074E-06 | 2.44884E-07 | 9.49144E-08 | 3.398E-07 | 1.394E-26 | 1.19E-26 | 3.5E-20 | 8.18E-20 | 8.8E-20 | 5.893E-20 | 1.00931E-08 | 1.3976E-06 |
| 120 | 5.169E-06 | 6.991E-06 | 2.44884E-07 | 1.77788E-07 | 4.227E-07 | 1.996E-28 | 1.48E-26 | 3.51E-26 | 7.12E-20 | 1.2E-19 | 8.151E-20 | 9.80125E-07 | 1.43893E-06 |
| 121 | 6.074E-06 | 6.991E-06 | 3.39798E-07 | 8.28738E-08 | 4.227E-07 | 2.777E-26 | 2.42E-28 | 5.72E-26 | 1.16E-19 | 1.4E-19 | 6.171E-20 | 9.43705E-07 | 1.47818E-06 |
| 122 | 5.169E-06 | 6.074E-06 | 1.19735E-07 | 9.49144E-08 | 2.148E-07 | 5.41E-27 | 4.62E-27 | 2.15E-26 | 3.03E-20 | 5.4E-20 | 4.518E-20 | 2.34687E-06 | 9.51786E-07 |
| 123 | 5.169E-06 | 6.991E-06 | 1.19735E-07 | 1.77788E-07 | 2.975E-07 | 8.631E-27 | 8.41E-27 | 2.16E-26 | 3.49E-20 | 6.7E-20 | 7.208E-20 | 1.7637E-06 | 1.07127E-06 |
| 124 | 6.074E-06 | 6.991E-06 | 2.14649E-07 | 8.28738E-08 | 2.975E-07 | 1.551E-26 | 1.35E-28 | 4.54E-26 | 7.35E-20 | 1E-19 | 7.228E-20 | 1.3246E-06 | 1.22358E-06 |
| 125 | 6.074E-06 | 6.991E-06 | 9.49144E-08 | 8.28738E-08 | 1.778E-07 | 4.94E-27 | 4.3E-27 | 2.42E-26 | 3.62E-20 | 6.1E-20 | 5.204E-20 | 1.0763E-06 | 1.32435E-06 |
| 126 | | | | | | | | | | | | | |

The steps used by an Excel computer program to solve equation (15) are shown in Table 6. The commands used in each Cell are given. As indicated above, the program shown in Table 6 is intended to be exemplary and it will be appreciated that other programs also can be utilized to solve the equations developed above.

TABLE 6

Program Steps

| Cell | Command | Comment (Copy as Formula) |
|---|---|---|
| I7 | =(H7 − H8) | Copy from Cell I7 to I12 |
| F9 | =((F7/F8)*F10*F5) | |
| E17 | =(M54*N91)/(M91*I54)) | Copy from Cell E17 to Cell E51 |
| F17 | =(M91) | Copy from Cell F17 to Cell F31 |
| F32 | =(M106 − D$91) | Copy from Cell F32 to Cell F41 |
| F42 | =(M116 − D$96) | Copy from Cell F42 to Cell F47 |
| F48 | =(M122 − D$100) | Copy from Cell F48 to Cell E50 |
| F51 | =(M125 − D$104) | |
| G17 | =(N91) | Copy from Cell G17 to Cell G31 |
| G32 | =(N106 + D$91) | Copy from Cell G32 to Cell G41 |
| G42 | =(N116 + D$96) | Copy from Cell G42 to Cell G47 |
| G48 | =(N122 + D$100) | Copy from Cell G48 to Cell G50 |
| G51 | =(N125 + D$104) | |
| H17 | =(N91/$F$10) | Copy from Cell H17 to Cell H51 |
| I17 | =(M91/$F$10) | Copy from Cell I17 to Cell I51 |
| J17 | =(I17 + H17) | Copy from Cell J17 to Cell J51 |
| K17 | =( − LOG(E17)) | Copy from Cell K17 to Cell K51 |
| L17 | =(F17 + G17)*$F$13) | Copy from Cell L17 to Cell L51 |
| M17 | =($F$9/F17 + G17)) | Copy from Cell M17 to Cell M51 |
| E54 | =($F$12) | Copy from Cell E54 to Cell E88 |
| F54 | =($H$7) | Copy from Cell F54 to Cell F68 |
| F69 | =($H$8) | Copy from Cell F69 to Cell F78 |
| F79 | =($H$9) | Copy from Cell F79 to Cell F84 |
| F85 | =($H$10) | Copy from Cell F85 to Cell F87 |
| F88 | =($H$11) | |
| G54 | =($H$8) | Copy from Cell G54 to Cell G58 |
| G59 | =($H$9) | Copy from Cell G59 to Cell G62 |
| G63 | =($H$10) | Copy from Cell G63 to Cell G65 |
| G66 | =($H$11) | Copy from Cell G66 to Cell G67 |
| G68 | =($H$12) | |
| G69 | =($H$9) | Copy from Cell G69 to Cell G72 |
| G73 | =($H$10) | Copy from Cell G73 to Cell G75 |
| G76 | =($H$11) | Copy from Cell G76 to Cell G77 |
| G78 | =($H$12) | |
| G79 | =($H$10) | Copy from Cell G79 to Cell G81 |
| G82 | =($H$11) | Copy from Cell G82 to Cell G83 |
| G84 | =($H$12) | |
| G85 | =($H$11) | Copy from Cell G85 to Cell G86 |
| G87 | =($H$12) | Copy from Cell G87 to Cell G88 |
| H54 | =($H$9) | |
| H55 | =($H$10) | Copy to Cells H59 and H69 |
| H56 | =($H$11) | Copy to Cells H60, H63, H70, H73, and H79 |
| H57 | =($H$12) | Copy to Cells H61, H64, H66, H71, H74, H76, H80, H82, and H85 |
| H58 | =($H$13) | Copy to Cells H62, H65, H67, H68, H72, H75, H77, H78, H81, H83, H84, H86, H87, and H88 |
| I54 | =($F$10 + ((B17 − 1)*E54*0.000001)) | Copy from Cell I54 to I88 |
| J54 | =(F$10 + ((C17 − 1)*E54*0.000001)) | Copy from Cell J54 to J88 |
| K54 | =($F$10 + ((D17 − 1)*E54*0.000001)) | Copy from K54 to K88 |
| L54 | =(F$11*B54*0.000001) | Copy from L54 to L88 |
| M54 | =(10^ − F54*I54) | Copy from M54 to M88 |
| B91 | =(10^ − G54*J54) | Copy from Cell B91 to B125 |
| C91 | =(10^ − H54*K54) | Copy from Cell C91 to C125 |
| D91 | =(10^ − F54*I54+(((17 − 1) − (B17 − 1))*L54) − (10^ − G54*J54)) | Copy from Cell D91 to D125 |
| E91 | =(10^ − G54*J54+(((17 − 1) − (C17 − 1))*L54) − (10^ − H54*K54)) | Copy from Cell E91 to E125 |
| F91 | =(D91 + E91) | Copy from Cell F91 to F125 |

TABLE 6-continued

Program Steps

| Cell | Command | Comment (Copy as Formula) |
|---|---|---|
| G91 | =(F91*C91*M54*D91*J54) | Copy from Cell G91 to G125 |
| H91 | =(M54*D91*B91*F91*K54) | Copy from Cell H91 to H125 |
| I91 | =(M54*D91*B91*K54) | Copy from Cell I91 to I125 |
| J91 | =(C91*I54*D91*B91) | Copy from Cell J91 to J125 |
| K91 | =(F91*C91*I54*B91) | Copy from Cell K91 to K125 |
| L91 | =(F91*C91*M54*J54) | Copy from Cell L91 to L125 |
| M91 | =((G91 − H91)/(I91 − J91 + K91 − L91)) | Copy from Cell M91 to M125 |
| N91 | =((M91*I54*D91*B91)/((M91*I54*B91) − (M54*(M91 + D91)*J54))) | Copy from Cell N91 to N125 |

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope. For example, while the invention has been described and illustrated in terms of analyzing fulciv acids, it will be appreciated that the invention also may be utilized to analyze other chemical solutions.

What is claimed is:

1. A method for determining equilibrium parameters for a macromolecule contained in a solution comprising the steps of:

(a) providing a solution containing the substance, the solution being in chemical equilibrium;

(b) measuring a known parameter of the solution;

(c) adding a predetermined amount of a standard solution to the original solution to form a modified solution;

(d) allowing the modified solution to reach chemical equilibrium;

(e) remeasuring the known parameter for the modified solution;

(f) repeating steps (c) through (e) for a predetermined number of iterations with the addition of the same standard solution in step (c) to the previously modified solution to obtain a plurality of measured values for the known solution parameter;

(g) determining a plurality of equations that include the original solution parameter and the directly measured values of the known solution parameter; and (h) solving simultaneously the plurality of equations to obtain at least one of the desired equilibrium parameters.

2. The method according to claim 1 wherein step (h) includes solving the plurality of equations simultaneously to determine all of the equilibrium parameters.

3. The method according to claim 2 wherein the desired equilibrium parameters include molecular weight and the measured known parameter is the pH of the solution.

4. The method according to claim 3 wherein the predetermined standard solution added to the original solution in steps (c) and (f) is an acid solution.

5. The method according to claim 3 wherein the predetermined standard solution added to the original solution in steps (c) and (f) is an alkaline solution.

6. The method according to claim 2 wherein the desired equilibrium parameters include $pK_a$ and the measured known parameter is the pH of the solution.

7. The method according to claim 2 wherein the desired equilibrium parameters include the stoichiometery of the solution and the measured known parameter is the pH of the solution.

8. The method according to claim 2 wherein the desired equilibrium parameters include molecular weight and the measured known parameter is a molar concentration of a known entity within the solution.

9. The method according to claim 2 wherein the desired equilibrium parameters include molar concentration and the measured known parameter is the pH of the solution.

10. The method according to claim 2 wherein the solution includes a metal and further wherein the measured known parameter is the pmetal of the solution.

11. The method according to claim 2 wherein the simultaneous solution of the equations in step (h) utilizes a computer program.

12. The method according to claim 2 wherein the following equilibrium equation is solved during step (h):

$$K_{eq}\left(m_{HY1} + \sum_{i=0}^{n-1} x_i\right)[V_1 + (n-1)V_s] - m_{H^+{}_n}\left(m_{Y^-1} - \sum_{i=0}^{n-1} x_i\right) = 0, n = 1, 2, 3 \ldots, x_o = 0_1$$

where:
  $K_{eq}$ is a constant of equivalency,
  n is the equilibrium iteration number,
  $m_{HY1}$ is the number of moles of solution provided in step (a),
  $V_1$ is the volume of the first solution,
  $V_3$ is the volume of standard solution,
  $m_{H^{\pm}{}_n}$ is the number of moles of H$^+$ in the standard solution, and
  $m_{Y^-{}_1}$ is the number of moles of Y$^-$ in the solution provided in step (a).

13. A method for determining the molecular weight of a substance contained in a solution comprising the steps of:
  (a) providing a first solution containing the substance, the first solution being in chemical equilibrium;
  (b) measuring a first pH of the first solution;
  (c) adding a predetermined amount of a standard solution to the original solution to form a second solution;
  (d) allowing the second solution to reach chemical equilibrium;
  (e) measuring a second pH of the second solution;
  (f) adding a predetermined amount of the same standard solution used in step (c) to the second solution to form a third solution;
  (g) allowing the third solution to reach chemical equilibrium;
  (h) measuring a third pH of the third solution; and
  (i) using the measured first, second and third pH's directly to calculate the molecular weight of the substance contained in the first solution.

14. The method according to claim 13 wherein the calculation in step (i) includes using the measured pH values to determine three equations and then subsequently simultaneously solving the equations.

15. The method according to claim 14 wherein the predetermined standard solution added to the original solution in steps (c) and (f) is an acid solution.

16. The method according to claim 14 wherein the predetermined standard solution added to the original solution in steps (c) and (f) is an alkaline solution.

17. The method according to claim 14 wherein the following equilibrium equation is solved (i):

$$K_{eq}\left(m_{HY1} + \sum_{i=0}^{n-1} x_i\right)[V_1 + (n-1)V_s] - m_{H^+{}_n}\left(m_{Y^-1} - \sum_{i=0}^{n-1} x_i\right) = 0, n = 1, 2, 3 \ldots, x_o = 0_1$$

where:
  $K_{eq}$ is a constant of equivalency,
  n is the equilibrium iteration number,
  $M_{HY1}$ is the number of moles of solution provided in step (a),
  $V_1$ is the volume of the first solution,
  $V_3$ is the volume of standard solution,
  $m_{H^{\pm}{}_n}$ is the number of moles of H$^+$ in the standard solution, and
  $m_{Y^{\times}{}_1}$ is the number of moles of Y$^-$ in the solution provided in step (a).

* * * * *

UNITED STATES PATENT AND TRADEMARK OFFICE
CERTIFICATE OF CORRECTION

| | | |
|---|---|---|
| PATENT NO. | : 6,745,132 B1 | |
| APPLICATION NO. | : 10/219684 | |
| DATED | : June 1, 2004 | |
| INVENTOR(S) | : Touradj Solouki et al. | |

It is certified that error appears in the above-identified patent and that said Letters Patent is hereby corrected as shown below:

Column 19, line 17, claim 12 should read:

12. The method according to claim 2 wherein the following equilibrium equation is solved during step (h):

$$K_{eq}(m_{HY_1} + \sum_{i=0}^{n-1} x_i)[V_1 + (n-1)V_S] - m_{H^+_n}(m_{Y^-_1} - \sum_{i=0}^{n-1} x_i) = 0, \quad n = 1,2,3..., \quad x_0 = [[0_1]]\underline{0}:$$

where:

$K_{eq}$ is a constant of equivalency, n is the equilibrium iteration number, $m_{HY1}$ is the number of moles of solution provided in step (a), $V_1$ is the volume of the first solution, $[[V_3]]\underline{V_s}$ is the volume of standard solution, $[[m_{H^+_n}^\pm]]\underline{m_{H^\pm_n}}$ is the number of moles of $H^+$ in the standard solution, and $m_{Y1}^-$ is the number of moles of $Y^-$ in the solution provided in step (a).

UNITED STATES PATENT AND TRADEMARK OFFICE
CERTIFICATE OF CORRECTION

| | | |
|---|---|---|
| PATENT NO. | : 6,745,132 B1 | |
| APPLICATION NO. | : 10/219684 | |
| DATED | : June 1, 2004 | |
| INVENTOR(S) | : Touradj Solouki et al. | |

It is certified that error appears in the above-identified patent and that said Letters Patent is hereby corrected as shown below:

Column 20, line 17, claim 23 should read:

17. The method according to claim 7 wherein the following equilibrium equation is solved during step (i):

$$K_{eq}(m_{HY_1} + \sum_{i=0}^{n-1} x_i)[V_1 + (n-1)V_s] - m_{H^+}(m_{Y^-_1} - \sum_{i=0}^{n-1} x_i) = 0 , \ n = 1,2,3... \ , \ x_0 = [[0_1]]\underline{0}:$$

where:

$K_{eq}$ is a constant of equivalency, n is the equilibrium iteration number, $m_{HY1}$ is the number of moles of solution provided in step (a), $V_1$ is the volume of the first solution, $V_s$ is the volume of standard solution, $[[m_{H^+n}^{\pm}]] \ \underline{m_{H^+n}^{\pm}}$ is the number of moles of $H^+$ in the standard solution, and $m_{Y1}^-$ is the number of moles of $Y^-$ in the solution provided in step (a).

Signed and Sealed this

Sixth Day of May, 2008

JON W. DUDAS
*Director of the United States Patent and Trademark Office*